(12) United States Patent
Deshpande et al.

(10) Patent No.: US 9,040,605 B2
(45) Date of Patent: May 26, 2015

(54) POLYMERIZATION PROCESS AND RAMAN ANALYSIS FOR OLEFIN-BASED POLYMERS

(75) Inventors: Kishori Deshpande, Lake Jackson, TX (US); Serena K. Stephenson, Lake Jackson, TX (US); Ravindra S. Dixit, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/991,832

(22) PCT Filed: Dec. 21, 2011

(86) PCT No.: PCT/US2011/066368
§ 371 (c)(1),
(2), (4) Date: Jun. 5, 2013

(87) PCT Pub. No.: WO2012/088217
PCT Pub. Date: Jun. 28, 2012

(65) Prior Publication Data
US 2013/0261224 A1 Oct. 3, 2013

Related U.S. Application Data

(60) Provisional application No. 61/425,601, filed on Dec. 21, 2010.

(51) Int. Cl.
*C08J 3/00* (2006.01)
*C08F 210/14* (2006.01)
*G01N 21/65* (2006.01)
*C08F 10/02* (2006.01)
*C08F 210/16* (2006.01)
*G01N 21/84* (2006.01)

(52) U.S. Cl.
CPC ............. *C08F 210/14* (2013.01); *C08F 210/16* (2013.01); *G01N 2021/8416* (2013.01); *C08F 2400/02* (2013.01); *G01N 2201/129* (2013.01); *G01N 21/65* (2013.01); *C08F 10/02* (2013.01)

(58) Field of Classification Search
USPC .................................................. 523/303, 300
See application file for complete search history.

(56) References Cited

U.S. PATENT DOCUMENTS

| 6,723,804 | B1 | 4/2004 | Battiste |
| 6,803,020 | B1 | 10/2004 | Agnely et al. |
| 2002/0156205 | A1 | 10/2002 | Long et al. |
| 2003/0130433 | A1 | 7/2003 | Wenz et al. |
| 2004/0176532 | A1 | 9/2004 | Buchholz et al. |
| 2006/0136149 | A1 | 6/2006 | Long et al. |

FOREIGN PATENT DOCUMENTS

WO 2004/063234 A1 7/2004

OTHER PUBLICATIONS

Bandermann, et al., Fourier-Transform Raman Spectroscopic On-Line Monitoring of Anionic Dispersion Block Copolymerization of Styrene and 1, 3-Butadiene, Macromolecular Rapid Communications, 2001, pp. 690-693, vol. 22.
Santos, et al., Online Monitoring of Suspension Polymerization Reactions Using Raman Spectroscopy, Industrial and Engineering Chemistry Research, 2004, pp. 7282-7289, vol. 43.
Reis, et al., Spectroscopic On-Line Monitoring of Reactions in Dispersed Medium: Chemometric Challenges, Analytica Chimica Acta, 2007, pp. 257-265, vol. 595.
Vieira, et al., Detection of Monomer Droplets in a Polymer Latex by Near-Infrared Spectroscopy, Polymer, 2001, pp. 8901-8906, vol. 42.
Jiang, et al., Chemometrics and Intelligent Laboratory Systems, 2004, pp. 83-92, vol. 70.
Witke, et al., Ramanspektroskopische Umsatzbestimmung Während der Suspensionspolymerisation von Vinylchlorid, Acta Polymerica, 1983, pp. 627-630, vol. 34, Abstract.
Sears, et al., Raman Scattering from Polymerizing Styrene. I. Vibrational Mode Analysis, Journal of Chemical Physics, 1981, pp. 1589-1598, vol. 75(4).
Sears, et al., Raman Scattering from Polymerizing Styrene. II. Intensity Changes as a Function of Conversion, Journal of Chemical Physics, 1981, pp. 1599-1602, vol. 75(4).
Chu, et al., Study of Thermal Polymerization of Styrene by Raman Scattering, Macromolecules, 1981, pp. 395-397, vol. 44.
PCT/US2011/066368, International Search Report, Apr. 18, 2012.
PCT/US2011/066368, International Preliminary Report on Patentability, Jul. 4, 2013.
PCT/US2011/066368, Written Opinion of the International Searching Authority, Apr. 18, 2012.

*Primary Examiner* — Edward Cain

(57) ABSTRACT

The invention provides a process for monitoring and/or adjusting a dispersion polymerization of an olefin-based polymer, the process comprising monitoring the concentration of the carbon-carbon unsaturations in the dispersion using Raman Spectroscopy. The invention also provides a process for polymerizing an olefin-based polymer, the process comprising polymerizing one or more monomer types, in the presence of at least one catalyst and at least one solvent, to form the polymer as a dispersed phase in the solvent; and monitoring the concentration of the carbon-carbon unsaturations in the dispersion using Raman Spectroscopy.

12 Claims, 9 Drawing Sheets

US 9,040,605 B2

POLYMERIZATION PROCESS AND RAMAN ANALYSIS FOR OLEFIN-BASED POLYMERS

REFERENCE TO RELATED APPLICATIONS

The present application is a 371 application of International Application No. PCT/US11/66368, filed on Dec. 21, 2011, which claims the benefit of U.S. Provisional Application No. 61/425,601, filed on Dec. 21, 2010.

BACKGROUND OF THE INVENTION

Dispersion polymerizations offer processing and energy advantages, but would require a new online analysis method for tracking monomer and/or comonomer incorporation into the polymer. Fourier transform near infrared (FTIR) spectroscopy, based on light transmission through the sample, is unable to monitor monomer concentration in presence of two phases due to scattering. There is a need for an on-line monitoring of a two phase polymerization system.

Bandermann et. al., *Fourier-Transform Raman Spectroscopic On-Line Monitoring of Anionic Dispersion Block Copolymerization of Styrene and 1,3-Butadiene*, Macromol. Rapid Commun, 2001, 22, pp. 690-693, discloses the use of Raman spectroscopy to monitor the anionic dispersion block copolymerization of styrene and 1,3-butadiene.

Santos et al., *Online Monitoring of Suspension Polymerization Reactions Using Raman Spectroscopy*, Ind. Eng. Chem. Res., 2004, 43, pp. 7282-7289, discloses the use of Raman spectroscopy to monitor aqueous suspension polymerizations.

Additional polymerizations monitored by Raman spectroscopy or other spectroscopy are disclosed in the following references: U.S. Pat. Nos. 6,803,020 and 6,723,804; U.S. Publication Nos. 2003/0130433 and 2004/0176532; International Publication No. WO2004/063234; and Reis et al., *Spectroscopic On-Line Monitoring of Reactions in Dispersed Medium: Chemometric Challenges*, Analytica Chimica Acta, 595 (2007), pp. 257-265; Vieira et al., *Detection of Monomer Droplets in a Polymer Latex by Near-Infrared Spectroscopy*, Polymer, 42 (2001), pp. 8901-8906; Jiang et al., *Resolution of Two-Way Data from On-Line Fourier—Transform Raman Spectroscopic Monitoring of the Anionic Dispersion Polymerization of Styrene and 1,3-Butadiene by Parallel Vector Analysis (PVA) and Window Factor Analysis (WFA)*, Chemometrics and Intelligent Laboratory Systems, 70 (2004), pp. 83-92; Witke et al., *Ramanspektroskopische Umsatzbestimmung Während der Suspensionspolymerisation von Vinylchlorid*, Acta. Polymerica, 34, pp. 627-630 (1983), Abstract; Sears et al., *Raman Scattering from Polymerizing Styrene. I. Vibrational Mode Analysis*, J. Chem. Phys., 75(4), 1981, pp. 1589-1598; Sears et al., *Raman Scattering from Polymerizing Styrene. II. Intensity Changes as a Function of Conversion*, J. Chem. Phys., 75(4), 1981, pp. 1599-1602; and Chu et al., *Study of Thermal Polymerization of Styrene by Raman Scattering*, Macromolecules, 1981, 14, pp. 395-397.

As discussed above, there is a need for on-line process control of a two phase polymerization system. There is a further need for an analytical method that will enable on-line process control, by simultaneously monitoring both the monomer and co-monomer concentrations in both the phases, thus permitting on-line process control. There is a further need for spectroscopy will be used in a non-aqueous, two-phase polymerization process at temperatures up to 200° C., or more, and pressures up to 10 MPa (100 bar). These needs and others have been met by the following invention.

SUMMARY OF INVENTION

The invention provides a process for monitoring and/or adjusting a dispersion polymerization of an olefin-based polymer, the process comprising monitoring the concentration of the carbon-carbon unsaturations in the dispersion using Raman Spectroscopy.

The invention also provides a process for polymerizing an olefin-based polymer in a dispersion, the process comprising polymerizing one or more monomer types, in the presence of at least one catalyst and at least one solvent, to form the polymer as a dispersed phase in the solvent; and monitoring the concentration of the carbon-carbon unsaturations in the dispersion using Raman Spectroscopy.

DETAILED DESCRIPTION

It has been discovered that the inventive processes described herein, can be used to polymerize and monitor non-aqueous, two-phase polymerization process, at temperatures up to 200° C., or more, and pressures up to 10 MPa (100 bar). The inventive process can be used to monitor both monomer and comonomer concentrations in both the phases, simultaneously, thus permits on-line process control. This invention can be applied to other polymers synthesized using a two phase dispersion polymerization. This includes polymers with ethylene, propylene, octene, and other α-olefin monomer/co-monomer units.

Figure 1:
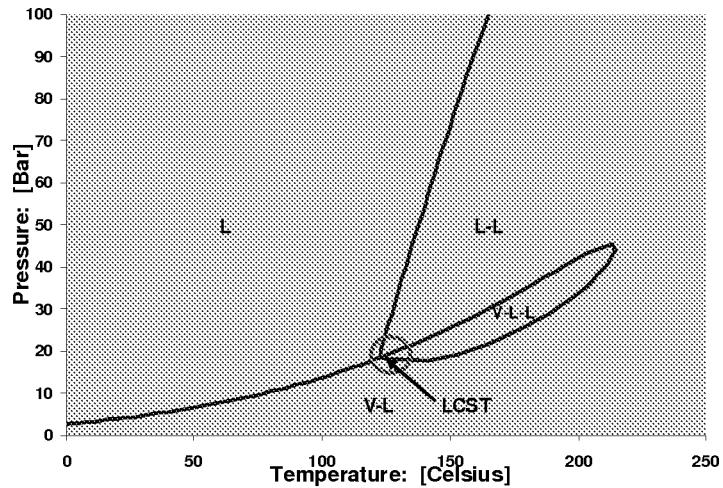
FIG. 1 is a phase diagram of a polymer-solvent system.

In a dispersion polymerization, the reactor operates above a critical temperature and pressure, inducing poor solubility for the polymer in an appropriate solvent. This limited solvent solubility, above the lower critical solution temperature (LCST), leads to two liquid phases, and thus enables economical product separation (for example, see FIG. 1). However, conventional analytical techniques, such as FTIR, essential for process control, fail for multi-phase systems. It has been discovered that the current invention will allow for a precise on-line process control, in a high temperature and high pressure polymer synthesis.

The inventive processes can be used in a hydrocarbon solvent-based, homogeneously catalyzed polymerization process. The inventive processes allow for the simultaneous monitoring of both monomer and co-monomer composition in a multi-phase system. This enables better process control of a two-phase, solvent-based polymerization process.

As discussed above, the invention provides a process for monitoring and/or adjusting a dispersion polymerization of an olefin-based polymer, the process comprising monitoring the concentration of the carbon-carbon unsaturations in the dispersion using Raman Spectroscopy.

An inventive process may comprise a combination of two or more embodiments described herein.

In one embodiment, the process monitors the dispersion polymerization.

In one embodiment, the process adjusts the dispersion polymerization.

In one embodiment, the process monitors and adjusts the dispersion polymerization.

In one embodiment, one or more monomer types are polymerized, in the presence of at least one catalyst and at least one solvent, to form a polymer, and wherein the polymer forms a dispersed phase in the solvent.

The invention also provides a process for polymerizing an olefin-based polymer, the process comprising polymerizing one or more monomer types, in the presence of at least one catalyst and at least one solvent, to form the polymer as a dispersed phase in the solvent; and monitoring the concentration of the carbon-carbon unsaturations in the dispersion using Raman Spectroscopy.

An inventive process may comprise a combination of two or more embodiments as described herein.

The following embodiments apply to all the inventive aspects discussed above.

In one embodiment, the at least one catalyst is soluble in the at least one solvent In one embodiment, the at least one solvent is a hydrocarbon.

In one embodiment, the process further comprises monitoring the vibrational spectra of the olefin-based polymer.

In one embodiment, the dispersion is in contact with a Raman probe.

In one embodiment, wherein during the Raman spectroscopy, a Raman spectrum is generated by a control computer.

In one embodiment, the Raman spectrum is processed using a chemometric model to determine the concentration of the carbon-carbon unsaturations in the dispersion, and/or and the amount of incorporation of one or more monomer types in the olefin-based polymer.

In one embodiment, the concentration of the carbon-carbon unsaturations and/or the amount of monomer(s) incorporation is fed back to a process control system.

In one embodiment, the control system, based on the carbon-carbon unsaturations and/or the amount of monomer(s) incorporation, monitors and/or adjusts monomer flow rate, catalyst flow rate, polymerization temperature, polymerization pressure, and/or polymer properties. Some examples of some polymer properties include density, melt index, molecular weight and molecular weight distribution.

The polymerization is not run in the supercritical region/conditions (or one phase). The polymerization is operated under subcritical region/conditions. In a further embodiment, the polymerization is run above the "lower critical solution temperature" and below the "cloud point pressure."

The polymerization is conducted in a region conducive for two liquid phase formation, typically at temperature and pressure higher than Lower Critical Solution Temperature (LCST). For example, see FIG. 1.

The polymerization is not an ionic polymerization, for example, a cationic polymerization or an anionic polymerization.

In a preferred embodiment, the dispersed phase is a liquid phase. In a further embodiment, the dispersion comprises at least two liquid phases, and preferably only two liquid phases.

In one embodiment, the polymerization is a continuous polymerization.

In one embodiment, the polymerization is a semi-batch polymerization.

The polymerization is not a solution polymerization.

In a preferred embodiment, the dispersion polymerization contains only two liquid phases.

The polymerization is not a slurry polymerization. Further, no particulate solids are formed in the polymerization reaction.

In a preferred embodiment, the polymerization does not comprise a fluorocarbon.

In a preferred embodiment, the polymerization does not comprise a fluorohydrocarbon.

In a preferred embodiment, the polymerization does not comprise water.

In a preferred embodiment, the polymerization does not comprise a suspending agent or a dispersing agent.

In a preferred embodiment, the polymerization does not comprise an emulsifier or a surfactant.

In a preferred embodiment, the polymerization does not comprise an ionic initiator.

In a preferred embodiment, the polymerization does not comprise a free radical initiator.

It is understood in the art, that three amounts of one or more impurities can be incorporated into a polymerization process.

In a preferred embodiment, the at least one catalyst is a single site catalyst.

In one embodiment, the catalyst is selected from metallocene catalysts, constrained geometry catalysts, and polyvalent anyloxyether compounds (post metallocene catalysts).

In one embodiment, the at least one catalysts is a post metallocene catalyst.

In one embodiment, the at least one catalysts is a constrained geometry catalyst.

In one embodiment, the polymerization comprises only one catalyst.

In one embodiment, catalyst selection allows polymerization at a temperature up to 220° C.

The catalyst preferably is not supported. The catalyst is completely soluble in the polymerization solvent.

In one embodiment, the polymerization is run at a pressure P and at a temperature T, and wherein T is greater than the lower critical solution temperature (LCST).

In one embodiment, the pressure P is less than, or equal to, the pressure at the cloud point at T.

In one embodiment, the T is less than, or equal to, the temperature at the bubble point at P.

In one embodiment, the T is less than, or equal to, 200° C., preferably less than, or equal to, 190° C.

In one embodiment, the P is less than, or equal to, 10 MPa, or less than, or equal to, 8 MPa.

In one embodiment, the polymerization pressure from 1 to 10 MPa, preferably from 1.5 to 8 MPa, more preferably from 2 to 5 MPa.

In one embodiment, the polymerization pressure from 5 to 7.5 MPa.

In one embodiment, the polymerization temperature is greater than the highest melting point of the polymer, as determined by DSC.

In one embodiment, the polymerization temperature is from 60° C. to 200° C., preferably from 80° C. to 200° C., and more preferably from 100° C. to 200° C., and even more preferably from 150° C. to 200° C.

In one embodiment, the polymerization temperature greater than 60° C., preferably greater than 80° C., and more preferably greater than 90° C.

In one embodiment, the polymerization temperature greater than 100° C., preferably greater than 120° C., and more preferably greater than 140° C.

An inventive process may comprise a combination of temperature and pressure as described herein.

In one embodiment, the one or more monomers are present in an amount less than, or equal to, 40 weight percent, based on the weight of the total weight of feed to the reactor.

In one embodiment, the one or more monomers are present in an amount less than, or equal to, 30 weight percent, based on the total weight of feed to the reactor.

In one embodiment, the feed to the polymerization comprises from 10 to 30 wt % of monomer (for example, ethylene); from 5 to 35 wt % of an α-olefin (for example, 1-octene); and 50 to 80 wt % of a hydrocarbon solvent (for example, isopentane).

In one embodiment, the polymer concentration in the polymerization is less than, or equal to, 60 weight percent, based on the total weight of the polymer dispersion.

In one embodiment, the polymer concentration in the polymerization is less than, or equal to, 50 weight percent, based on the total weight of the polymer dispersion.

In one embodiment, the polymer concentration in the polymerization is less than, or equal to, 40 weight percent, based on the total weight of the polymer dispersion.

In one embodiment, the effective viscosity of the reaction mixture less than, or equal to, 15 cP, preferably less than, or equal to, 10 cP, more preferably less than, or equal to, 6 cP.

In one embodiment, the polymerization takes place in a reactor configuration selected from the group consisting of the following: (a) one reactor and (b) two or more reactors configured in series.

In one embodiment each reactor is a stirred tank reactor. In a preferred embodiment, no gas phase is present in the reactor mixture under steady state conditions.

In a preferred embodiment, no molten polymer is present in the polymerization.

In a preferred embodiment, the polymerization does not contain a molten polymer.

In a preferred embodiment, the polymer dispersion comprises solvent, and polymer.

The invention also provides an apparatus for monitoring and/or adjusting a dispersion polymerization of any embodiment described herein, said apparatus comprising at least one reactor and at least one Raman probe.

An inventive process may comprise a combination of two or more embodiments as described herein.

An inventive apparatus may comprise a combination of two or more combinations described herein.

The invention also provides a polymer formed from an inventive process.

An inventive polymer may comprise a combination of two or more embodiments as described herein.

Raman Spectroscopy

A Raman spectrometer typically includes the following: a Raman probe, a laser source, a CCD camera, and a control computer. Examples of Raman probes include, but are not limited to, an immersion optic probe, a filter head, and fiber optic cables.

In one embodiment, the frequency range is from 300 to 3000 $cm^{-1}$.

In one embodiment, the Raman spectrum is generated by a control computer.

In one embodiment, the Raman Spectrum is processed using a chemometric model to determine the concentration of the carbon-carbon unsaturations in the dispersion, and/or and the amount of incorporation of one or more monomer types in the olefin-based polymer. Examples of chemometric models include, but are not limited to, partial least squares, classical least squares, and linear regressions.

In one embodiment, the concentration of the carbon-carbon unsaturations and/or the amount of monomer(s) incorporation is fed back, for example, via a controller (for example, a Siemen's controller), to a process control system, such as a feed control valve.

In one embodiment, the control system uses information from the spectrometer to monitor and/or adjust monomer flow rate, catalyst flow rate, polymerization temperature, polymerization pressure, and/or polymer properties.

In one embodiment, the Raman spectrometer comprises a 20-40 mW incident laser.

In one embodiment, the collection time is 10-25 seconds, preferably 10-20 seconds.

In one embodiment, the signal to noise ratio (S/N) if greater than 10, preferably greater than 15.

In one embodiment, the lower detection limit (LDL) is from 0.5-2 wt % monomer, based on signal to noise ratio and concentration.

Solvents/Monomers/Polymers

Solvents include, but are not limited to, one or more of C2-C24 alkenes, such as ethane, propane, n-butane, iso-butane, n-pentane, isopentane, n-hexane, iso-hexane, mixed hexanes, n-octane, iso-octane, mixed octanes, cyclopentane, cyclohexane, etc., single-ring aromatics, such as toluene and xylenes, and C4 to C150 isoparaffins.

Suitable solvent include, but are not limited to, those shown below in Table 1.

TABLE 1

| Solvents | | |
|---|---|---|
| Solvent | T (° C.) LCEP | P (Bar) LCEP |
| Methyl cyclohexane | 275 | 43 |
| Cyclohexane | 256.5 | 44.1 |
| Octane | 240 | 27.1 |
| 2-Methyl Heptane | 232 | 25.7 |
| Cyclopentane | 214 | 41.1 |
| Iso-Octane | 203 | 21.8 |
| Hexane | 175 | 21 |
| Iso-Hexane | 152.2 | 17.5 |
| Pentane | 148.4 | 21.8 |
| Iso-pentane | 110.4 | 14.3 |

*LCEP = Lower Critical End Point

The one or more monomers include, but are not limited to, ethylenically unsaturated monomers, conjugated or nonconjugated dienes, polyenes, and combinations thereof.

In one embodiment, the one or more monomers are selected from the group consisting of ethylene, C3-C20 α-olefins, styrene, alkyl-substituted styrene, dienes, naphthenics, and combinations thereof.

In one embodiment, the one or more monomers are selected from the group consisting of ethylene, C3-C20 α-olefins, styrene, alkyl-substituted styrene, dienes, and combinations thereof.

In one embodiment, the one or more monomers are selected from the group consisting of ethylene, C3-C20 α-olefins, dienes, and combinations thereof.

In one embodiment, the one or more monomers are selected from the group consisting of ethylene, C3-C20 α-olefins, and combinations thereof.

In one embodiment, the one or more monomers are selected from the group consisting of ethylene, C3-C10 α-olefins, and combinations thereof.

In one embodiment, the one or more monomers are ethylene, and a C3-C20 α-olefin, and preferably a C3-C10 α-olefin.

In one embodiment, the one or more monomers are ethylene and an α-olefin selected from the group consisting of propylene, 1-butene, 1-hexene, and 1-octene.

In one embodiment, the one or more monomers are ethylene, an α-olefin selected from the group consisting of propylene, 1-butene, 1-hexene, and 1-octene, and a diene.

In one embodiment, the one or more monomers are ethylene, propylene, and a diene, and preferably 5-ethylidene-2-norbornene (ENB).

In one embodiment, the one or more monomers are propylene, and ethylene or a C3-C20 α-olefin, and preferably a C3-C10 α-olefin.

In one embodiment, the one or more monomers are propylene, and ethylene.

In one embodiment, the polymer is an ethylene-based polymer. In a further embodiment, the ethylene-based polymer is an ethylene/α-olefin/diene interpolymer or an ethylene/α-olefin interpolymer.

In one embodiment, the olefin-based polymer is an ethylene-based polymer or a propylene-based polymer.

In one embodiment, the olefin-based polymer is an ethylene-based polymer.

In one embodiment, the olefin-based polymer is a propylene-based polymer.

In one embodiment, the polymer is present in an amount from 30 to 40 weight percent, based on total weight of the reactor contents.

In one embodiment, the polymer has a density from 0.86 to 0.92 g/cc.

An olefin-based polymer may comprise a combination of two or more embodiments described herein.

An ethylene-based polymer may comprise a combination of two or more embodiments described herein.

A propylene-based polymer may comprise a combination of two or more embodiments described herein.

Ethylene/α-Olefin/Diene Interpolymers

The ethylene/α-olefin/diene interpolymers have polymerized therein C2 (ethylene), at least one α-olefin and a diene. Suitable examples of α-olefins include the C3-C20 α-olefins. Suitable examples of dienes include the C4-C40 non-conjugated dienes.

The α-olefin is preferably a C3-C20 α-olefin, preferably a C3-C16 α-olefin, and more preferably a C3-C10 α-olefin. Preferred C3-C10 α-olefins are selected from the group consisting of propylene, 1-butene, 1-hexene and 1-octene, and more preferably propylene. In a preferred embodiment, the interpolymer is an EPDM. In a further embodiment, the diene is 5-ethylidene-2-norbornene (ENB).

In one embodiment, the diene is a C6-C15 straight chain, branched chain or cyclic hydrocarbon diene. Illustrative non-conjugated dienes are straight chain, acyclic dienes, such as 1,4-hexadiene and 1,5-heptadiene; branched chain, acyclic dienes, such as 5-methyl-1,4-hexadiene, 2-methyl-1,5-hexadiene, 6-methyl-1,5-heptadiene, 7-methyl-1,6-octadiene, 3,7-dimethyl-1,6-octadiene, 3,7-dimethyl-1,7-octadiene, 5,7-dimethyl-1,7-octadiene, 1,9-decadiene, and mixed isomers of dihydromyrcene; single ring alicyclic dienes, such as 1,4-cyclohexadiene, 1,5-cyclooctadiene and 1,5-cyclododecadiene; multi-ring alicyclic fused and bridged ring dienes, such as tetrahydroindene, methyl tetrahydroindene; alkenyl, alkylidene, cycloalkenyl and cycloalkylidene norbornenes, such as 5-methylene-2-norbornene (MNB), 5-ethylidene-2-norbornene (ENB), 5-vinyl-2-norbornene, 5-propenyl-2-norbornene, 5-isopropylidene-2-norbornene, 5-(4-cyclopentenyl)-2-norbornene, and 5-cyclohexylidene-2-norbornene. The diene is preferably a non-conjugated diene selected from ENB, dicyclopentadiene, 1,4-hexadiene, or 7-methyl-1,6-octadiene, and preferably, ENB, dicyclopentadiene or 1,4-hexadiene, more preferably ENB or dicyclopentadiene, and even more preferably ENB.

In a preferred embodiment, the ethylene/α-olefin/diene interpolymer comprises a majority amount of polymerized ethylene, based on the weight of the interpolymer.

An ethylene/α-olefin interpolymer may comprise a combination of two or more embodiments described herein.

Ethylene/α-Olefin Interpolymers

Ethylene/α-olefin interpolymers include polymers formed by polymerizing ethylene with one or more, and preferably one, C3-C10 α-olefin(s). Illustrative α-olefins include propylene, 1-butene, 1-pentene, 1-hexene, 4-methyl-1-pentene, 1-heptene, 1-octene, 1-nonene and 1-decene. Preferably, the α-olefin is propylene, 1-butene, 1-hexene or 1-octene. Preferred copolymers include ethylene/propylene (EP) copolymers, ethylene/butene (EB) copolymers, ethylene/hexene (EH) copolymers, ethylene/octene (EO) copolymers.

An ethylene/α-olefin interpolymer may comprise a combination of two or more embodiments as described herein.

Propylene-Based Polymers

In one embodiment, the polymer is a propylene-based polymer. In a further embodiment, the propylene-based polymer is a propylene/α-olefin interpolymer, and preferably a copolymer, or a propylene/ethylene interpolymer, and preferably a copolymer.

Preferred comonomers include, but are not limited to, C2 and C4-C20 α-olefins, and preferably C2 and C4-C10 α-olefins. Preferred comonomers include ethylene, 1-butene, 1-pentene, 1-hexene, 1-heptene and 1-octene, and more preferably include ethylene, 1-butene, 1-hexene and 1-octene, and even more preferably ethylene.

A propylene-based polymer may comprise a combination of two or more embodiments as described herein.

DEFINITIONS

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter.

The term "interpolymer," as used herein, refers to polymers prepared by the polymerization of at least two different types of monomers. The generic term interpolymer thus includes copolymers (employed to refer to polymers prepared from two different types of monomers), and polymers prepared from more than two different types of monomers.

The term "olefin-based polymer," as used herein, refers to a polymer that contains at least a majority weight percent, based on the weight of the polymer, polymerized olefin (for example, ethylene or propylene), and, optionally, one or more additional comonomers.

The term "ethylene-based polymer," as used herein, refers to a polymer that contains at least a majority weight percent polymerized ethylene (based on the weight of polymer), and, optionally, one or more additional comonomers.

The term "propylene-based polymer," as used herein, refers to a polymer that contains at least a majority weight percent polymerized propylene (based on the weight of polymer), and, optionally, one or more additional comonomers.

The term "polymer-rich phase," as used herein, in relation to two or more phases under consideration, refers to the phase containing the greater concentration of polymer, as measured by its weight fraction, based on the total weight of this phase.

The term "solvent-rich phase," as used herein, in relation to two or more phases under consideration, refers to the phase containing the greater concentration of solvent as measured by its weight fraction, based on total weight of this phase.

The term "phase," as used herein, refers to is a region of space (a thermodynamic system), throughout which all physical properties of a material are uniform. Examples of physical properties include density, index of refraction, and chemical composition.

A liquid-liquid phase is a combination of two separate liquid phases, which are not miscible.

The term "solvent," as used herein, refers to a substance (for example, a hydrocarbon (excluding monomer and comonomer)) that dissolves a species of interest, like a monomer and/or catalyst, resulting in a liquid phase.

The term "hydrocarbon," as used herein, refers to a chemical compound or molecule that contains only hydrogen and carbon atoms.

The term "dispersion polymerization," as used herein, refers to a polymerization process, in which the formed polymer is insoluble in the polymerization solvent.

The term "solution polymerization," as used herein, refers to a polymerization process, in which the formed polymer is dissolved in the polymerization solvent.

Lower Critical Solution Temperature (LCST), as used herein, is defined as the temperature, above which, a solution of fixed composition, at a fixed pressure, separates into two liquid phases, and, below this temperature, the solution exists as a single liquid phase.

The term "polymerization system," as used herein, refers to a mixture comprising monomers, solvent and catalyst, and which will undergo polymerization reaction under appropriate conditions. The polymerization system corresponds to the total feed to the reactor.

The term "adiabatic reactor," as used herein, refers to a reactor which has no active heat removal mechanism and no active heat addition mechanism.

The term "single phase polymer solution," as used herein, refers to the complete dissolution of polymer in one or more solvents (typically much lower in molecular weight than polymer) to form a homogeneous (most often in liquid state) phase.

The phrase "concentration of polymer in the polymer-rich phase," as used herein, refers to the weight fraction of the polymer, based on the total weight of the solution containing the polymer (polymer-rich phase).

The phrase "concentration of polymer in the solvent-rich phase," as used herein, refers to the weight fraction of the polymer, based on the total weight of the solution containing the polymer (solvent-rich phase).

The term "subcritical region," as defined herein, refers to a polymerization temperature below the critical temperature of the polymerization medium (defined as the mixture of solvent(s), monomer and comonomer(s) (no catalyst(s) or cocatalyst(s)), and a polymerization pressure below the critical pressure of the polymerization medium.

The term "critical temperature," as used herein, refers to the temperature of the polymerization medium, above which, the polymerization medium does not phase separate, regardless of any pressure change.

The term "critical pressure," as used herein, refers to the pressure of the polymerization medium, above which, the polymerization medium does not phase separate, regardless of any temperature change.

The term "cloud point pressure," are used herein, refers to the pressure, below which, the polymer solution of a fixed composition at a fixed temperature, separates into two liquid phases. Above this pressure, the polymer solution is a single liquid phase.

The term "cloud point temperature," as used herein, refers to the temperature (threshold temperature) above which, the polymer solution of a fixed composition at a fixed pressure, separates into two liquid phases. Below this temperature, the polymer solution is a single liquid phase. In addition, the cloud point temperature may also be a ceiling temperature, below which, two phases exist, and above which, one phase exists.

The term "bubble point pressure," as used herein, refers to that pressure, at constant temperature, at which, for a two liquid phase solution, a first bubble of vapor appears.

The term "effective viscosity," as used herein, refers to the viscosity of a dispersion, containing two or more liquid phases, as calculated by the fraction of each phase, and where a dense phase is fully dispersed in a continuous phase.

The phrase "catalyst soluble in the solvent," as used herein, refers to the amount of catalyst that can be dissolved in the solvent.

The term "dispersed phase," as used herein, refers to the undissolved liquid that is distributed in a solvent or continuous phase.

The term "reaction mixture," as used herein, refers to all the chemical contents in a reactor, such as monomer, comonomers, solvent, any amount of polymer or no polymer, and/or catalyst. Before a polymerization reaction begins, typically no polymer is present in the reactor.

The phrase "total weight of feed to the reactor," as used herein, refers to the total amount (weight) components, such as monomer, comonomer, solvent, hydrogen and/or catalyst, which are added to the respective reactor.

The phrase "steady state conditions," as used herein, refers to the reactor conditions when the variable under consideration, such as temperature, composition shows no change with respect to time.

The term "monomer type," as used herein, refers to the chemical composition and number of carbon atoms in a monomer.

The phrase "adjusting the dispersion polymerization," as used herein, refers to measuring one or more reactor conditions, and sending the measured information to a control system, which, in turn, sends out-put to make the appropriate change(s) to one or more reactor condition(s) to level(s) within desired limits.

The phrase "monitoring a dispersion polymerization," as used herein, refers to measuring the reaction parameters, such as, for example, temperature, pressure and/or monomer concentration, in the reactor, to ensure that the measured parameters are within the desired limits.

The phrase "fed back," as used herein, refers to a process, where the data from one or more reactor condition(s) is/are sent to a process control system.

The term "process control system," as used herein, refers to a device/machine capable of receiving input from other devise(s)/machine(s), and which can use such input to change reactor conditions.

The terms "comprising", "including", "having" and their derivatives are not intended to exclude the presence of any additional component, step or procedure, whether or not the same is specifically disclosed. In contrast, the term, "consisting essentially of" excludes from the scope of any succeeding recitation any other component, step or procedure, excepting those that are not essential to operability. The term "consisting of" excludes any component, step or procedure not specifically delineated or listed.

Test Methods

Raman Spectroscopy

A RXN1 Raman system from Kaiser Optical Systems, Inc. (KOSI) was used to monitor the polymerizations. The specifications for this particular system were as follows:

Class IIIb 785 nm Invictus laser with peak output power of 400 mW.

Computer controlled laser shutter and laser output power control.

USB connected camera.

MR probe head with laser interlock and fiber optic connection to the laser and camera.

Immersion optic (18" long, ½" diameter) with a short focal length.

The data collection software was iCRaman. The probe head was attached to the end of the "18" long, ½" diameter" immersion optic, and the immersion optic was inserted through the top of the reactor, to a depth just above the mixing blades, and secured via a Swagelok fitting. The tip of the immersion optic is located approximately ½ inch from the cooling/heating coil inside the reactor.

The laser power output directly at the laser was set to 160 mW, but dropped to approximately 85 mW, when aligned properly, at the end of the long run of fiber optic cable. Approximately another "factor of 2" of power loss was expected by the time the light reached the tip of the immersion optic. Therefore, the sample inside the reactor was exposed to approximately 40 mW of power when the laser was on, and the laser shutter was open.

Spectra were collected every 10-12 seconds, and every spectrum was saved in its raw form (.spc extension) for future model building and analysis. Spectral collection began at the beginning of the batch polymerization, or when there was sample in the reactor to be analyzed. A short spectral collection time was selected because of the speed of the reaction in the semi-batch reactor after the addition of catalyst.

The "signal to noise (S/N)" ratios (calculated as the peak height divided by the RMS error of the surrounding baseline) are shown in Table 2.

TABLE 2

| For example batches: | S/N |
|---|---|
| initial octene batch 1 | 20 |
| initial octene batch 2 | 25 |
| initial ethylene batch 1 | 26 |
| initial ethylene batch 2 | 26 |
| final octene batch 1 | 23 |
| final octene batch 2 | 39 |
| final ethylene batch 1 | 12 |
| final ethylene batch 2 | 17 |

11% octene in isopentane (no polymer present) - S/N 50
4% ethylene in isopentane (no polymer present) - S/N 19

The lower detection limits with these collection parameters (LDL defined as a peak S/N of >3) were estimated by calculating the S/N ratios for a series of concentrations of ethylene and octene in isopentane, and then generating "S/N versus concentration" plots, and fitting a trend line, forcing it through the zero intercept. The resulting line is used to calculate the concentrations that would correspond to an S/N of 3 (for ethylene, the LDL is approximately 0.6 wt %, and for octene, the LDL is approximately 1.8 wt %; each wt % is based on a regression of the "signal to noise" versus concentration plot.

Raman spectra of several batch polymerizations are shown in FIGS. 2-5.

Figure 2:
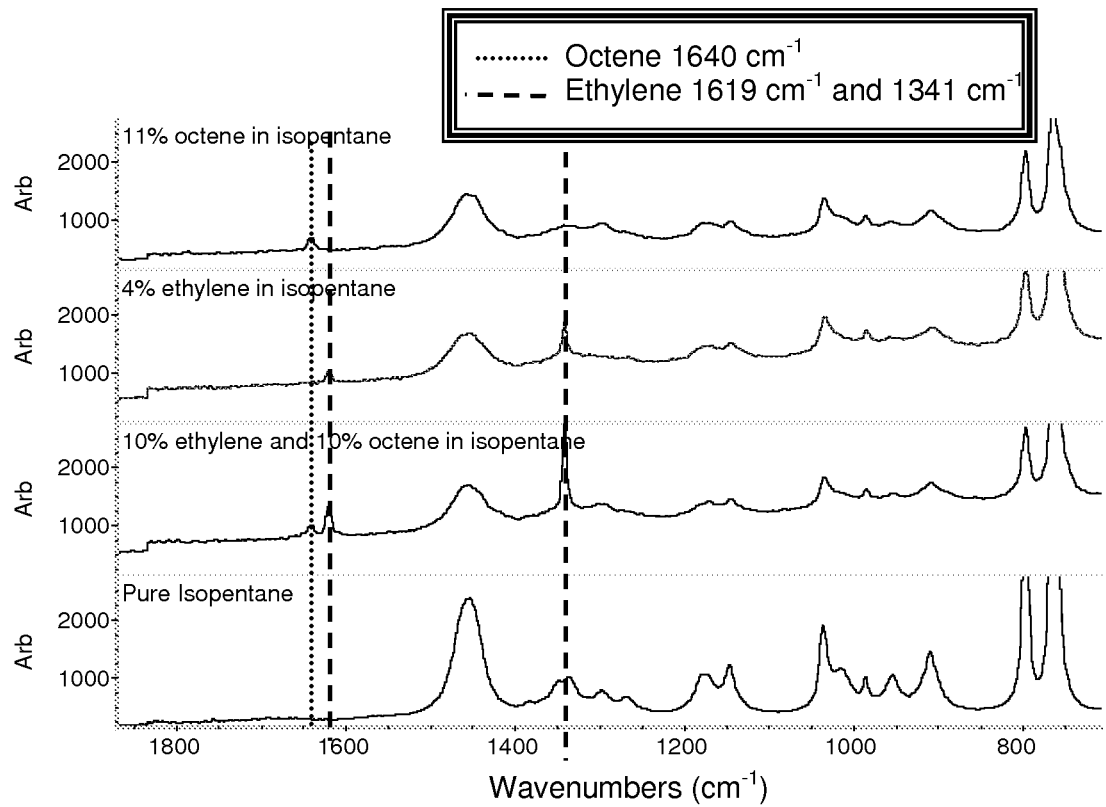
FIG. 2 is an overlay of Raman spectra of pure solvent (isopentane) and comonomer/solvent mixtures showing primary comonomer peaks of interest (700-1900 cm-1 range).

FIG. 2 is an overlay of Raman spectra of pure solvent (isopentane) and comonomer/solvent mixtures showing primary comonomer peaks of interest (500-1900 cm$^{-1}$ range). These spectra do not have polymer so are single phase liquids.

Figure 3:
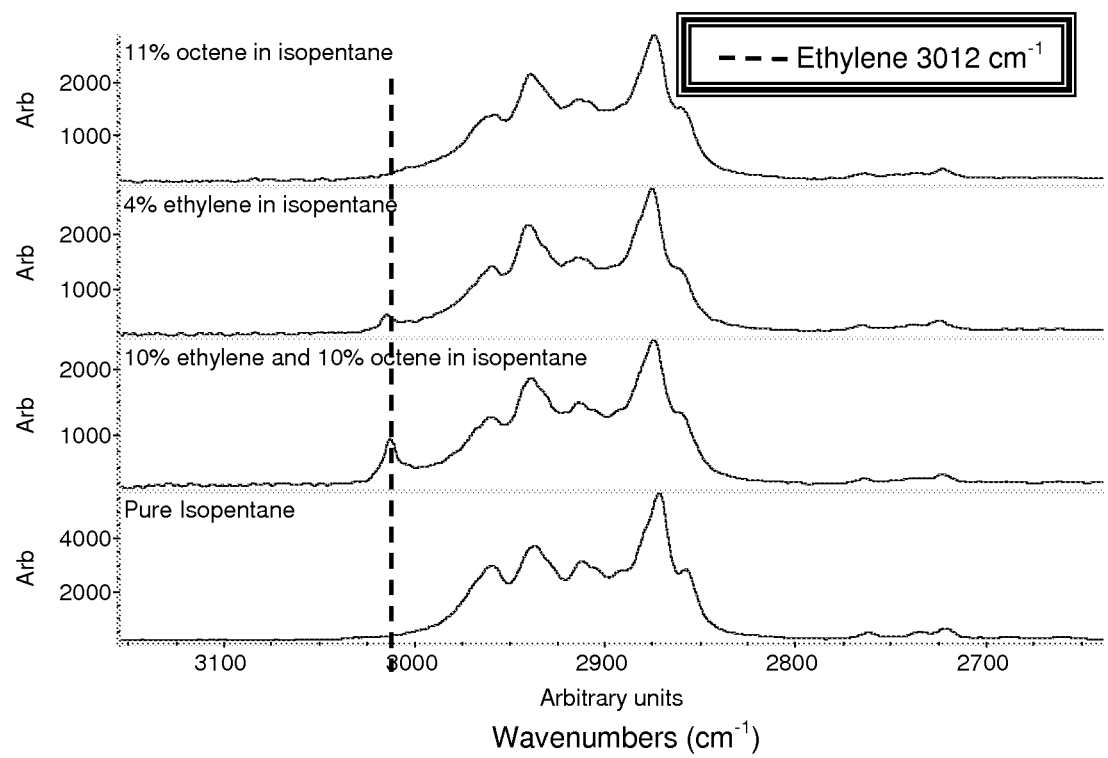
FIG. 3 is an overlay of Raman spectra of pure solvent (isopentane) and comonomer/solvent mixtures showing primary comonomer peak of interest (2600-3150 cm-1 range).
Figure 4:
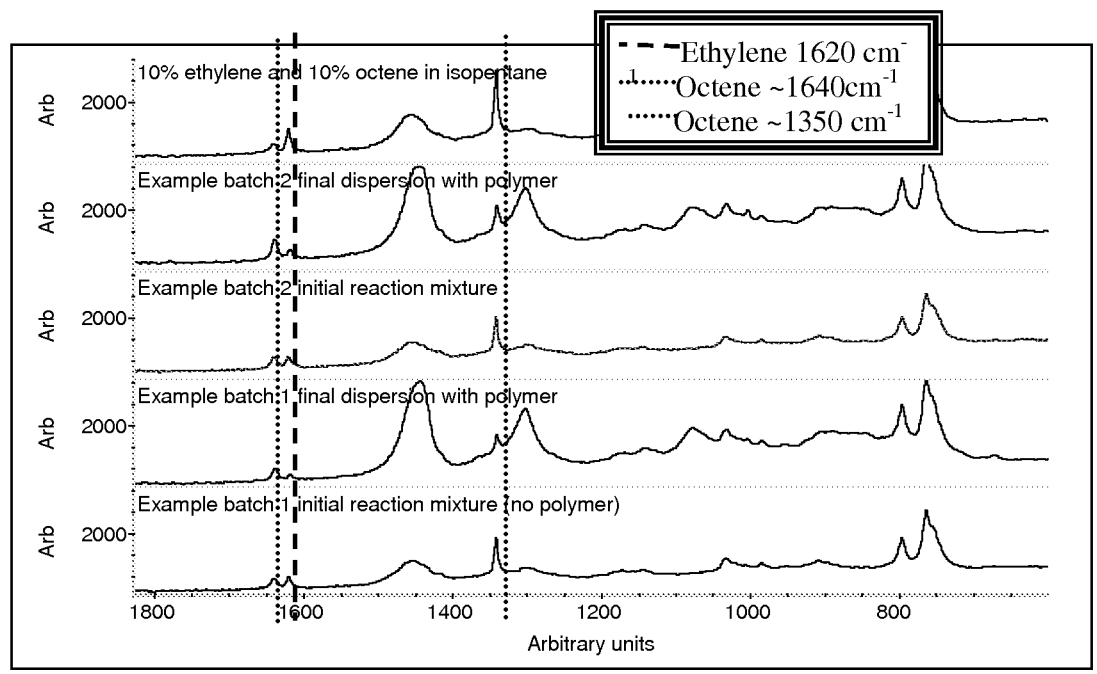
FIG. 4 is an overlay of Raman spectra of comonomer/solvent mixture, initial reaction mixture (no polymer) and final reaction dispersion containing polymer (600-1800 cm-1 range).

FIG. 3 is an overlay of Raman spectra of pure solvent (isopentane) and comonomer/solvent mixtures showing primary comonomer peak of interest (2600-3200 cm$^{-1}$ range). These spectra do not have polymer so are single phase liquids FIG. 4 is an overlay of Raman spectra of comonomer/solvent mixture, initial reaction mixture (no polymer) and final reaction dispersion containing polymer (500-1900 cm$^{-1}$ range).

Figure 5:
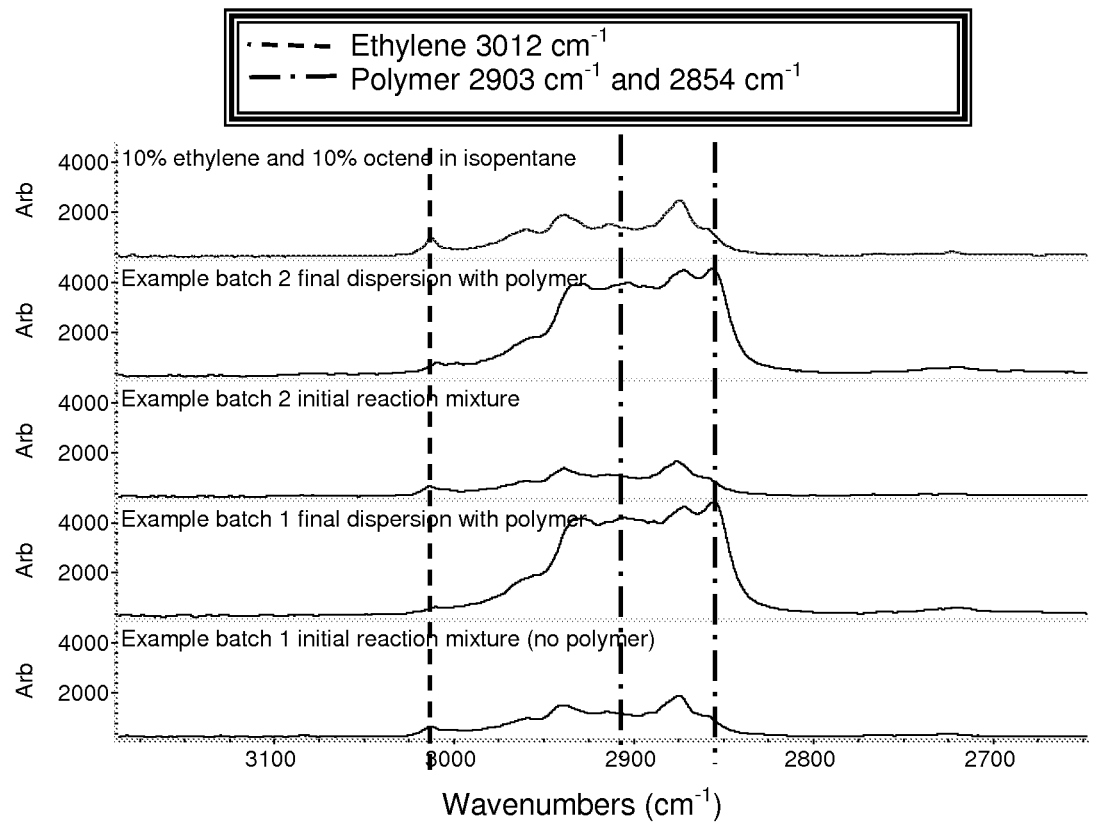
FIG. 5 is an overlay of Raman spectra of comonomer/solvent mixture, initial reaction mixture (no polymer) and final reaction dispersion containing polymer (2600-3200 cm-1 range).

FIG. 5 is an overlay of Raman spectra of comonomer/solvent mixture, initial reaction mixture (no polymer) and final reaction dispersion containing polymer (2600-3200 cm$^{-1}$ range).

A PLS (Partial Least Squares) model was created to directly model octene incorporation in the polymer, without going through the intermediate of prediction of octene consumption first. Several spectra from the end of each isopentane reactor run were used as inputs to the model, for a total of 54 included spectra. A spectral region from 544 to 1720 cm$^{-1}$ was used. This region not only includes the ethylene and octene transitions, but also a large amount of polymer backbone and solvent information, in order to focus on the polymer composition, and not the concentrations of the monomers. The actual octene incorporation values ranged from approximately 15 wt % octene in the polymer to approximately 38 wt % octene in the polymer, and the model was independent of the starting, or ending, octene monomer concentrations. Each weight percent was based on the actual weight of the polymer.

Figure 6:
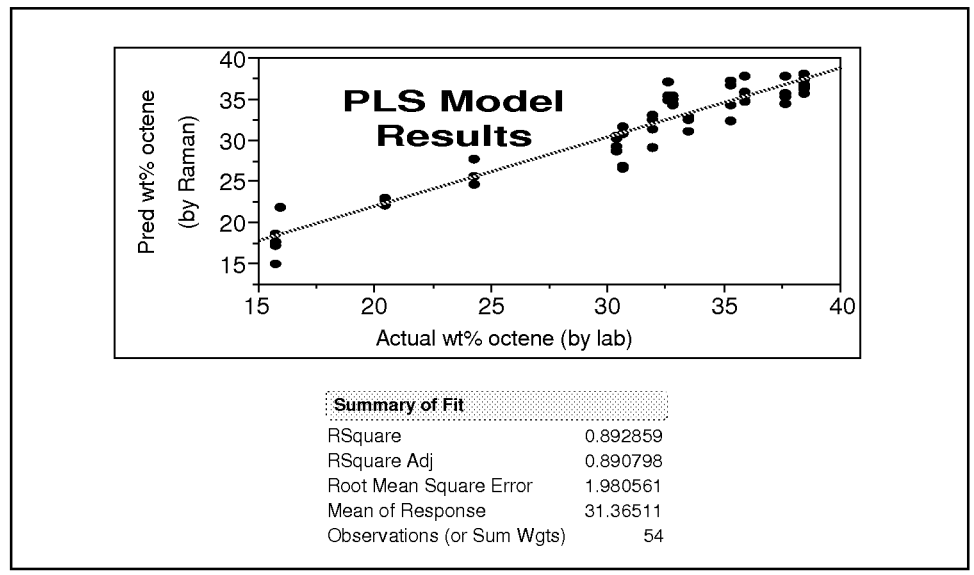
FIG. 6 is a plot representing the direct prediction of wt % octene incorporation in the polymer from Raman spectroscopy versus the actual wt % of octene incorporation as determined by a FTNIR reference method.

A plot of the "prediction wt % octene versus the actual wt % octene" for the model is shown in FIG. 6. The standard error of cross validation (SECV) indicates the predictive capability of the model. Here, the SECV is 2.2 wt %, so the concentration of octene incorporated in the polymer is within approximately 4.4 wt % octene incorporation.

Molecular Weight and Molecular Weight Distribution: GPC (Gel Permeation Chromatography)

For Gel Permeation Chromatography (GPC) measurements, the chromatographic system used was a Polymer Laboratories Model PL-210. The column and carousel compartments were operated at 145° C. Four Polymer Laboratories, 20-um, Mixed-A LS columns were used with a solvent of 1,2,4-trichlorobenzene (TCB). The samples were prepared at a concentration of "0.1 g of polymer in 50 ml of solvent." The solvent used to prepare the sample contained 200 ppm of the antioxidant butylated hydroxytoluene (BHT). Samples were prepared by agitating lightly for 1-2 hours at 160° C. The injection volume was 200 microliters, and the flow rate was 1.0 ml/min Calibration of the GPC column set was performed with narrow molecular weight distribution, polystyrene standards, purchased from Varian Inc. (previously Polymer Laboratories). The polystyrene standard peak molecular weights were converted to polyethylene molecular weights using T. Williams and I. M. Ward, "The Construction of Polyethylene Calibration Curve for Gel Permeation Chromatography Using Polystyrene Fractions," J. Polym. Sci. Polym. Lett., 6, 631 (1968), incorporated herein by reference.

Density

Density was measured in accordance with ASTM D 792-08. About 16 g of polymer material was pressed (Monarch ASTM Hydraulic Press—Model No. CMG30H-12-ASTM) into a "one inch×one inch" die. The sample was pressed at 190° C., at 5600 lbf, for six minutes. Then the pressure was increased to 15 tonf, while simultaneously cooling the sample from 190° C. to 30° C., at 15° C./minute.

Octene Incorporation

Octene incorporation was measured using Nicolet Magna 560 spectrometer. Thin films of the calibration material, approximately 0.05-0.14 mm in thickness, were prepared by compression molding the polymer sample between Teflon coated sheets or aluminum foil. It was important that the films had a matte finish, to avoid interference fringes, when the films were examined in transmission mode on a FT-IR spectrometer. The absorbance of each standard was collected using 32 scans in the background. A sample spectra were collected, with a resolution of 4 $cm^{-1}$ or lower, 1 level of zero filling, and Happ-Genzel apodization function. The obtained spectra (standard) were baseline corrected at 2450 $cm^{-1}$. The second derivative of the normalized absorbance spectra was calculated over 4000-400 $cm^{-1}$ interval. To generate the calibration curve, the "peak-to-peak values" of the second derivative spectra for the controlled samples were calculated over the 1390-1363 $cm^{-1}$ interval, recorded, and plotted against the weight percent octene in each polymer control, as determined by 13C NMR. The octene levels in the polymers prepared herein were calculated using a calibration curve.

Experimental

Representative Polymerization of an Ethylene/Octene Copolymer

A semi-batch reactor, controlled using a Siemen's controller, was used in the polymerization. First, octene was added to the reactor at a flow rate of 160 g/min Next solvent (iso-pentane) was added at a rate of 400 g/minute. The reactor was subsequently heated to 140° C., using electrical band heaters. Next, hydrogen was added at 160 sccm (standard cubic centimeters), followed by ethylene addition, at an amount required to reach the desired reactor pressure (450-750 psig). The octene, solvent, and hydrogen additions were each controlled using a flow controller. The ethylene addition was controlled using a pressure regulator.

The reaction mixture was stirred continuously at 1400 rpm to maintain homogenous conditions. To start the polymerization, a solution containing the catalyst, cocatalyst and a scavenger, was automatically injected at 8 ml/min, using a high pressure reciprocating pump (Accuflow Series II), rated up to 1500 psi. The catalyst was zirconium, dimethyl[(2,2'''-[1,3-propanediylbis(oxy-kO)]bis[3'',5,5''-tris(1,1-dimethylethyl)-5'-methyl[1,1':3',1''-terphenyl]-2'-olato-kO)]](2-)]-, (OC-6-33)-). See International Publication No. WO 2007/136494 (Cat. A11), fully incorporated herein by reference. This catalyst was activated using a tetrapentafluorophenylborate cocatalyst. A modified methylalumoxane was used as a scavenger.

Figure 7:
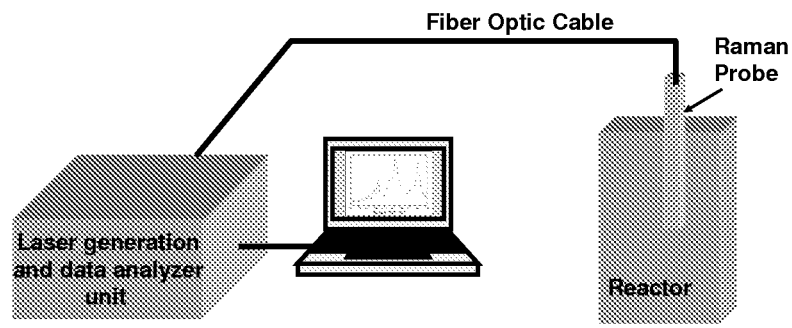
FIG. 7 is a schematic of a Raman system (a) and Raman Probe (b) installed in a semi-batch reactor.
Figure 8:
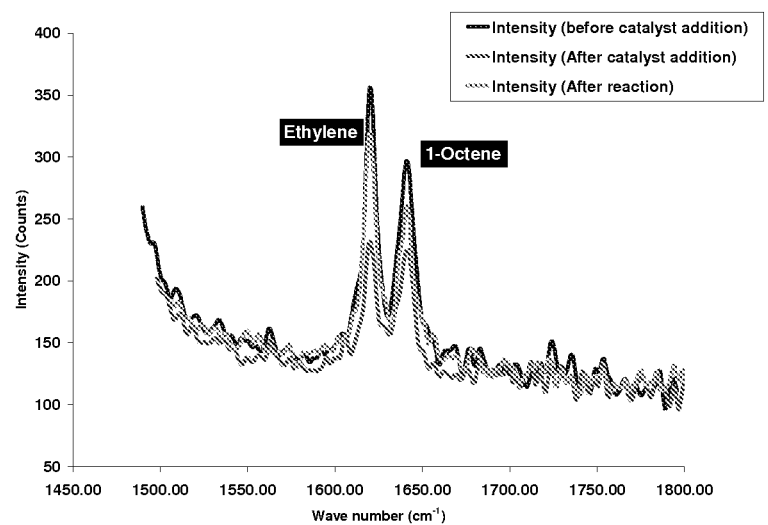
FIG. 8 is an overlay of Raman spectra for monomer(ethylene) and comonomer (1-octene) during a polymerization.

FIG. 7 further illustrates the above polymerization. As discussed, Raman spectroscopy was used to monitor ethylene polymerization in iso-pentane solvent. The ethylene feed concentration was 7.7 wt %, and the 1-octene was fed at 13.7 wt %. Each weight percentage is based on the weight of the reactor contents. The ethylene/octene copolymer was obtained using the above catalyst, at 140° C. and 3 MPa (30 bar), in a one gallon, semi-batch reactor. A Raman probe was installed into the reactor to obtain Raman spectra of the process (see FIG. 8). As shown in FIG. 8, the ethylene and octene show distinct Raman shifts at 1621 $cm^{-1}$ and 1642 $cm^{-1}$, respectively. Further, the intensity of the peaks decrease upon reaction completion, because of the lower reactant concentrations.

The polymerization was completed in about ten minutes, and the polymer was dumped, at 140° C. into a product kettle located under the reactor. The polymer sample was isolated, washed, and dried. Results from this polymerization are shown in Table 3 (see batch #1).

Figure 9:
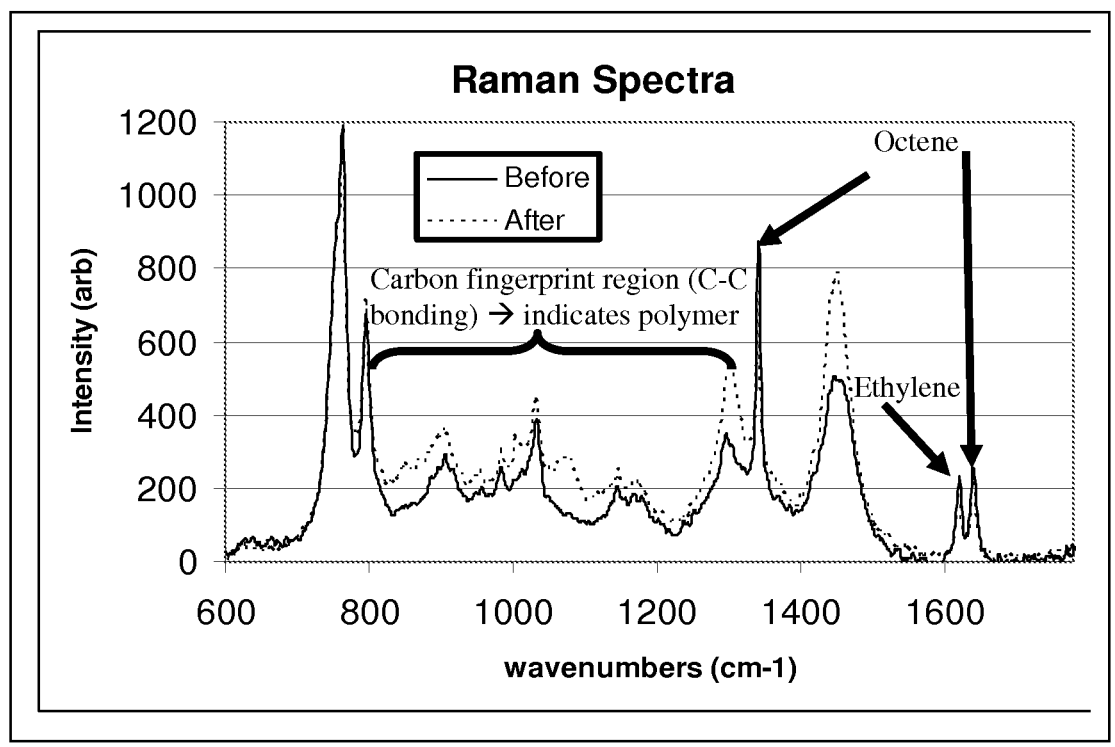
FIG. 9 depicts the Raman spectra for a dispersion polymerization, before and after polymerization.
Figure 10:
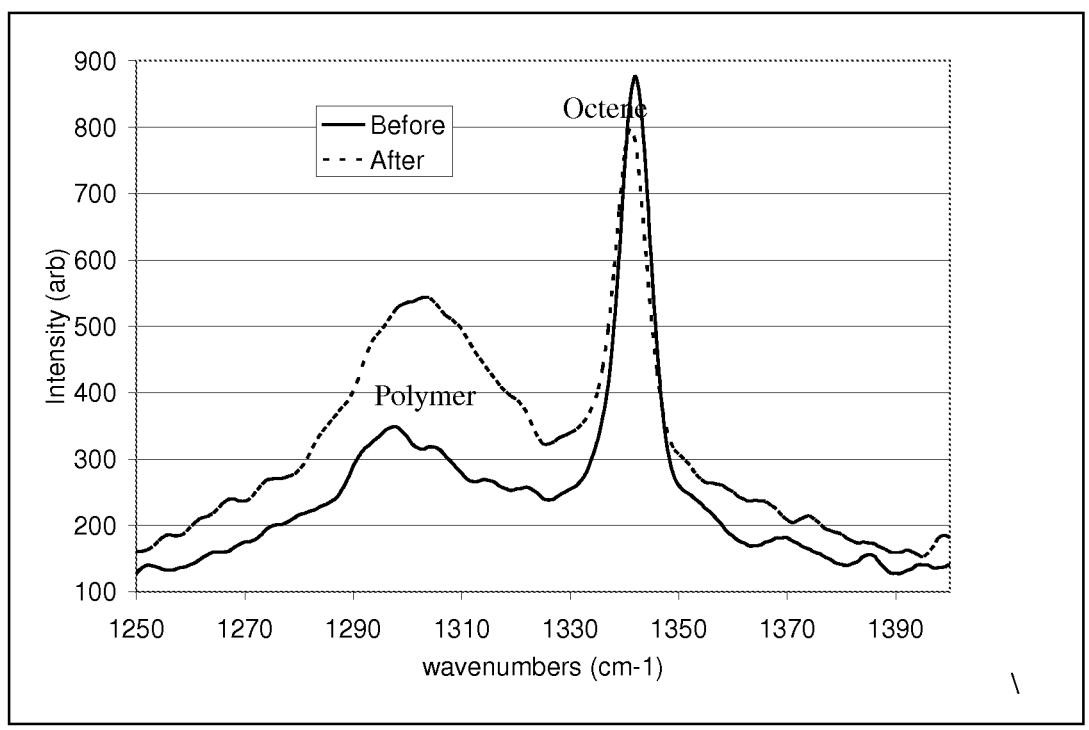
FIG. 10 depicts the expansion of the octene peak of FIG. 9 before and after polymerization.
Figure 11:
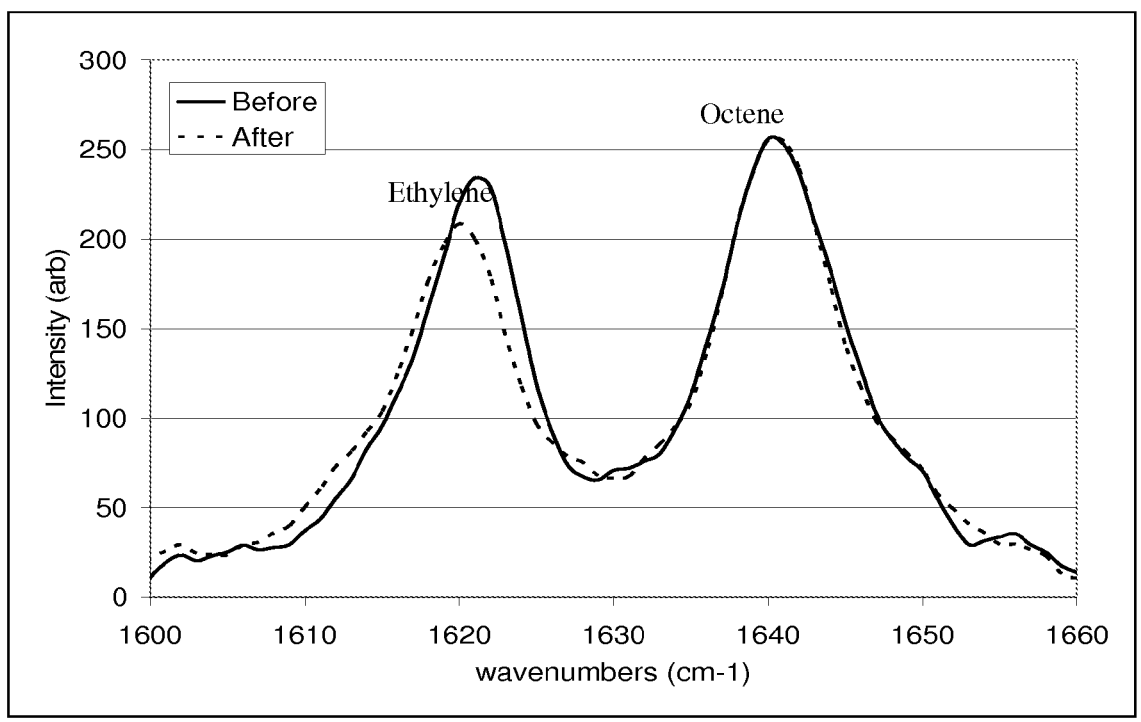
FIG. 11 depicts the expansion of the ethylene peak of FIG. 9 before and after polymerization.

Raw Raman spectra are collected using the Raman spectrometer. Examples Raman spectra, before, and after, the addition of catalyst are shown in FIG. 9. Simple observation of these spectra show differences before and after the formation of polymer. Namely, there is a lot more intensity in the C—C fingerprint region between 800 and 1500 $cm^{-1}$ in the "after" spectra than there is in the "before" spectra, due to the formation of C—C bonds during polymerization. Also note that the intensities of the octene transition at ~1350 $cm^{-1}$ and the ethylene/octene C=C transitions just above 1600 $cm^{-1}$ are smaller after completion of the polymerization, as compared to the intensities of these peaks before polymerization. This is a second indicator that a reaction has taken place, and octene/ethylene has been consumed in the production of polymer with C—C bonds. FIGS. 10 and 11 show expansions of the octene and ethylene peaks before and after the reaction.

In order to move from the qualitative picture of visual inspection of spectra to a useful quantitative result, which can be used in reaction monitoring and feedback process control, a Partial Least Squares (PLS) chemometric model was used. Models were generated using the Grams PLS/IQ toolbox, using the entire spectral region from 544 to 1720 $cm^{-1}$, in order to incorporate both reactant and product information into the predictive model, to provide more accurate results. PLS modeling is well understood by those skilled in chemometrics, and detailed information can be found in any of a number of good textbooks (for example, K. R. Beebe, R. J. Pell, M. B. Seasholtz, *Chemometrics A Practical Guide*; John Wiley & Sons, Inc, 1998).

Table 3 summarizes the batch polymerization runs used as calibrations for the Raman studies. Columns for the batch number, the mmoles of hydrogen added and the mol % octene added to the reactor, as determined by a mass flow meter, are provided. Also, laboratory analysis results of the resultant molecular weight, octene incorporation, and density are provided. Variations in molecular weight were made by adjusting the hydrogen level. For variations in density, the hydrogen loading was held constant (120 mmol), and the octene to ethylene ratio in the reactor was changed. The octene level was varied in batches #16 to #20. The PLS model was used to directly correlate spectra with wt % octene incorporation in the polymer.

After creation and validation of the chemometric model, the model was applied in real-time to the collected spectra. In the example here, the prediction is the wt % of octene incorporated into the polymer. If too much, or too little, octene is incorporated, the reaction parameter, such as addition quantities, flow rates, pressures and temperatures are adjust accordingly to move the "wt % octane" values into the targeted range.

TABLE 3

Feed compositions and polymer characteristic results for molecular weight and density.

| Batch # | mmol Hydrogen | Mol % Octene | Molecular Weight $M_W$ | wt % octene incorporation into polymer (lab) | Density (gm/cc) | Wt % octene incorporation into polymer (Raman) |
|---|---|---|---|---|---|---|
| 1 | 20 | ~14 | 316360 | 20.42 | 0.8826 | 22.0 |
| 2 | 20 | ~14 | 316220 | 24.99 | 0.8826 | 23.5 |
| 3 | 20 | ~14 | 298480 | 26.01 | 0.8828 | 26.9 |
| 4 | 10 | 14.9 | 342730 | 31.07 | 0.8727 | N/A |
| 5 | 10 | 14.9 | 376080 | 30.37 | 0.8751 | 29.6 |
| 6 | 20 | 14.8 | 255980 | 33.47 | 0.8625 | N/A |
| 7 | 20 | ~15 | 251930 | 34.14 | 0.8564 | N/A |
| 8 | 30 | ~15 | 213700 | 32.58 | 0.871 | 34.3 |
| 9 | 30 | ~15 | 216200 | 33.5 | 0.8706 | 32.7 |
| 10 | 50 | ~15 | 217480 | 35.93 | 0.8704 | 36.5 |
| 11 | 50 | ~15 | 128700 | 37.68 | 0.868 | 37.9 |
| 12 | 75 | ~15 | 106170 | 35.32 | 0.8714 | 35.0 |
| 13 | 75 | ~15 | 75600 | 38.43 | 0.8683 | 37.4 |
| 14 | 120 | ~15 | 89110 | 32.78 | 0.8712 | 35.1 |
| 15 | 120 | ~15 | 87680 | 38.46 | 0.8699 | 36.9 |
| 16 | 120 | 14.89 | 70530 | 31.96 | 0.8572 | N/A |
| 17 | 120 | 14.54 | 65500 | 30.68 | 0.8579 | N/A |
| 18 | 120 | 8.80 | 67000 | 24.30 | 0.8586 | N/A |
| 19 | 120 | 4.61 | 91620 | 15.96 | 0.9035 | N/A |
| 20 | 120 | 4.46 | 10130 | 15.73 | 0.9018 | N/A |

Figure 12:
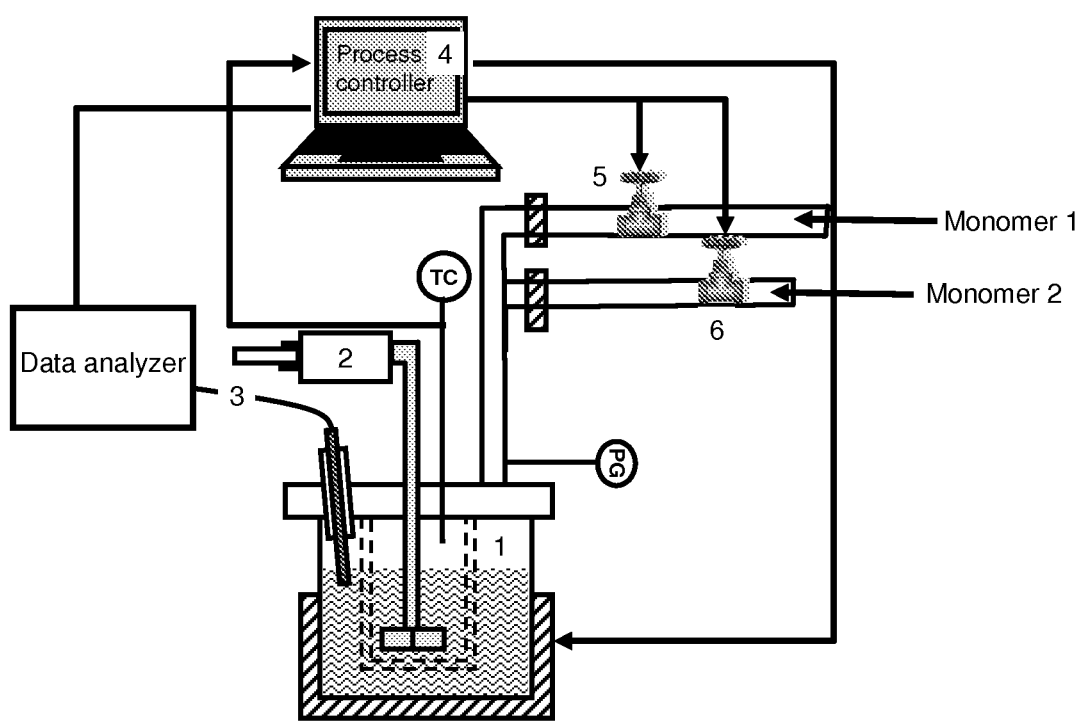
FIG. 12 is a schematic showing an "on-line" process control for a dispersion polymerization.

As discussed above, the invention can be used to monitor the overall monomer/co-monomer composition in the reactor. One can use the inventive process for adjusting a dispersion polymerization. For example, FIG. 12 shows a schematic for on-line process control for dispersion polymerization. A typical set-up may include a reactor 1, which is equipped with a thermocouple (TC) and pressure guage (PG). The agitator 2, ensures a well-mixed two phase system. The Raman probe 3, monitors the reactor for overall monomer concentration in both phases, with the help of a data analyzer, and transmits this information to the process controller (4). This information is then used to control the monomer feed valves 5 and 6, to adjust the monomer feed rate to the reactor, and thereby control the polymerization reaction.

Although the invention has been described in considerable detail in the preceding examples, this detail is for the purpose of illustration, and is not to be construed as a limitation on the invention as described in the following claims.

The invention claimed is:

1. A process for monitoring and/or adjusting a dispersion polymerization of an olefin-based polymer, the process comprising monitoring the concentration of the carbon-carbon unsaturations in the dispersion using Raman Spectroscopy; and wherein, in the dispersion polymerization, one or more monomer types are polymerized, in the presence of at least one catalyst and at least one solvent, to form a polymer, and wherein the polymer forms a dispersed phase in the solvent; and wherein the at least one catalyst is soluble in the at least one solvent.

2. The process of claim 1, wherein the temperature of the polymerization is from 60° C. to 200° C.

3. The process of claim 1, wherein the pressure of the polymerization is from 1 to 10 MPa.

4. The process of claim 1, wherein the at least one solvent is a hydrocarbon.

5. The process of claim 1, wherein the process further comprises monitoring the vibrational spectra of the olefin-based polymer.

6. The process of claim 1, wherein the dispersion is in contact with a Raman probe.

7. The process of claim 1, wherein, during the Raman spectroscopy, a Raman spectrum is generated by a control computer.

8. The process of claim 7, wherein the Raman spectrum is processed using a chemometric model to determine the concentration of the carbon-carbon unsaturations in the dispersion, and/or and the amount of incorporation of one or more monomer types in the olefin-based polymer.

9. The process of claim 8, wherein the concentration of the carbon-carbon unsaturations and/or the amount of monomer(s) incorporation is fed back to a process control system.

10. The process of claim 9, wherein the process control system, based on the carbon-carbon unsaturations and/or the amount of monomer(s) incorporation, monitors and/or adjusts monomer flow rate, catalyst flow rate, polymerization temperature, polymerization pressure, and/or polymer properties.

11. A process for polymerizing an olefin-based polymer, the process comprising polymerizing one or more monomer types, in the presence of at least one catalyst and at least one solvent, to form the polymer as a dispersed phase in the solvent; and monitoring the concentration of the carbon-carbon unsaturations in the dispersion using Raman Spectroscopy; and wherein the at least one catalyst is soluble in the at least one solvent.

12. The process of claim 11, wherein the at least one solvent is a hydrocarbon.

* * * * *